United States Patent [19]

Sjöstrand

[11] Patent Number: 4,788,331
[45] Date of Patent: Nov. 29, 1988

[54] METHOD OF PREPARING 5-AMINO SALICYLIC ACID

[75] Inventor: Ulf Sjöstrand, Karlskoga, Sweden

[73] Assignee: Nobel Kemi AB, Karlskoga, Sweden

[21] Appl. No.: 79,591

[22] Filed: Jul. 7, 1987

[30] Foreign Application Priority Data

Jul. 7, 1986 [SE] Sweden ................................ 8603007

[51] Int. Cl.⁴ ............................................... C07C 99/00
[52] U.S. Cl. ..................................... 562/453; 534/674; 260/508
[58] Field of Search ......................... 562/453; 534/674; 200/508

[56] References Cited

U.S. PATENT DOCUMENTS

| 1,542,265 | 6/1925 | Norris et al. | 562/453 |
| 1,727,468 | 9/1929 | Kammerer | 534/674 |
| 2,658,673 | 11/1953 | Terpstra | 562/453 |
| 3,063,980 | 11/1962 | Bloom et al. | 260/508 |
| 4,256,634 | 3/1981 | Goebel et al. | 534/674 |

FOREIGN PATENT DOCUMENTS 1159919  6/1985  U.S.S.R. .............................. 562/453

OTHER PUBLICATIONS

Ginsburg, "Concerning Amines", pp. 21–22 (1968).
Sal'nikova et al., Chem. Abst; vol. 72, #99759a (1970).

Primary Examiner—James H. Reamer
Attorney, Agent, or Firm—Pollock, Vande Sande & Priddy

[57] ABSTRACT

The disclosure relates to a method of producing 5-amino salicylic acid from salicylic acid, with sulphanilic acid as the recyclable auxiliary chemical.

The method according to the present invention includes linking between the diazonium salt of the sulphanilic acid and the salicylic acid, followed by a splitting by hydrogenation with hydrogen gas and catalyst, and selective precipitation of the desired product.

7 Claims, No Drawings

METHOD OF PREPARING 5-AMINO SALICYLIC ACID

TECHNICAL FIELD

The present invention relates to a novel method of preparing 5-amino salicylic acid (5-ASA) from salicylic acid, with sulphanilic acid as the auxiliary chemical. The reaction carried out according to the present invention by linking and splitting gives, as its final product, an extremely pure 5-amino salicylic acid well suited for pharmaceutical preparation.

BACKGROUND ART 5-amino salicylic acid (5-ASA) has previously been produced from, for instance, 3-nitrobenzoic acid which is partially reduced to the corresponding hydroxylamine, which is converted in an acidic environment to 5-ASA (Ref. 1 and 2). However, the difficulties involved in purifying thus produced 5-ASA of undesired isomers restricts the usability of the method for producing pharmaceutical qualities.

Attempts have also been made in this art to produce 5-ASA by nitration of salicylic acid, but in such a method, considerable amounts of 3-isomers are obtained, which drastically reduces product yield and results in an impure end product (Ref. 3).

A further method of producing 5-ASA by reaction of carbon dioxide with p-aminophenol under high pressure, a so-called Kolbe reaction is described in the literature in this art (Ref. 4). However, this method requires access to high pressure equipment, and, furthermore, the toxicity of the p-aminophenol restricts the usability of this method from purely practical points of view.

Finally, it is previously known in the art that 5-ASA may also be produced by direct amination of salicylic acid by diazonium linking and splitting of the thus formed azo compounds. This method has also been employed in production of 5-ASA on an industrial scale. In such production, aniline (Ref. 5) is normally employed as the source of the diazonium salt, thus the use of sulphanilic acid is also described in the literature in the art (Ref. 6). For splitting of the azo bonds, use has been made of dithionite or any analogous sulphur compound which has been added in such excessive amount that this has entailed a considerable hazard to the immediate environment in the industrial production of 5-ASA. According to a recently published method (Ref. 7) the azo compound obtained according to the above method may also be split electro-chemically in a basic environment. However, this method can only be used by manufacturers who have access to the highly specialized equipment required for industrial electro-chemical synthesis.

It follows that all of the above-described methods for the production of 5-ASA suffer from manifest shortcomings either in the form of high contents of undesirable isomers in the end product paired with low product yield, or in the form of stringent requirements in respect to the handling of environmentally hazardous chemicals, or alternatively the need of expensive and complex specialized equipment.

OBJECT OF THE PRESENT INVENTION

The object of the present invention is to offer a novel method for the production of 5-ASA which may be carried out using standard production equipment and which neither requires the handling of toxic discharge chemicals nor results in environmentally hazardous waste, and which gives a final substance of high pharmaceutical purity.

SUMMARY OF THE INVENTION

According to the present invention, 5-amino salicylic acid is, thus, produced from salicylic acid with sulphanilic acid as the recyclable auxiliary chemical. Thus, the double sodium salt of the salicylic acid is reacted in a previously known manner with the diazonium salt of sulphanilic acid, whereupon the thus obtained 5-(p-sulphophenylazo)salicylic acid is split by hydrogenation with hydrogen gas and a catalyst at elevated pressure, and a temperature of 40°–60° C., whereafter the thus obtained 5-amino salicylic acid is precipitated from the mother liquor by acidification thereof to a pH at which the 5-amino salicylic acid is precipitated, but not the recovered sulphanilic acid, which, in its turn, is precipitated at a later stage in the process by further acidification of the mother liquor.

DESCRIPTION OF PREFERRED EMBODIMENT

According to the present invention, requisite amounts of sulphanilic acid or a salt thereof are slurried in water, a strong acid, preferably sulphuric acid or hydrochloric acid, being added to the solution in such an amount that at least three hydrogen ions correspond to each equivalent sulphanilic acid. Thereafter, slightly more than one mole equivalent of sodium nitrite dissolved in water is added.

The sodium nitrite is added at a temperature which does not appreciably exceed 20° C., since the desired diazonium salt begins to break up at approximately this temperature. The thus started diazoting is then allowed to react to completion before the thus produced diazonium salt is further employed.

Furthermore, to a solution of sodium hydroxide in water, there is separately added salicylic acid in such an amount that it is present as a double sodium salt. To this salt, there is subsequently added the produced diazonium salt at a regulated temperature which, during addition phase, is kept below 20° C. so as to avoid break-up of the diazonium salt.

Once all additions have been completed, the reaction is allowed to proceed to completion and since elevated temperature will hasten the reaction, the reaction temperature may now be permitted to rise to 20°–25° C.

At this reaction stage, it is appropriate that the salicylic acid in the form of its double sodium salt be present in a certain mole surplus in relation to the sulphanilic acid.

The above described reaction gives, as end product, 5-(p-sulphophenyl azo) salicylic acid, which is a per se previously known product which may also be produced by other means and which has been put to certain uses previously, for example as a colorant.

The thus obtained 5-(p-sulphophenyl azo) salicylic acid may now, according to the present invention, be split by hydrogenation with hydrogen gas in the presence of a preferably palladium or platinum based catalyst. The 5-(p-sulphophenyl azo) salicylic acid is, here, mixed with an amount of catalyst adapted to conform to the available cooling capacity (the reaction is slightly exothermic), whereafter the mixture is exposed to excess pressure of hydrogen gas as long as hydrogen gas continues to be absorbed. The pressure of the hydrogenation is not particularly critical but we have found that it is practical to carry out said hydrogenation at an elevated pressure of about 1-10 atm above the atmospheric pressure. In order to obtain a reasonable reaction time, the temperature should exceed 50° C. in this stage.

When no hydrogen gas is consumed, the splitting reaction according to the present invention may be considred as completed and the catalyst is filtered off at unchanged temperature. The splitting reaction according to the present invention gives sodium sulphanilate and 5-amino salicylic acid. By a thickening of the system and by slowly cooling to approx 20° C., the thus formed sodium sulphanilate can, to a certain degree, be precipitated and filtered off, since its solubility at this temperature has been exceeded.

In order to ensure a complete splitting of 5-(p-sulphophenyl azo) salicylic acid, it may be appropriate to heat the thus obtained filtrate to approx 60° C. in a nitrogen gas atmosphere and to add, under agitation, a minor amount (or up to 5 percent by weight) of sodium dithionite dissolved in water. This amount of sodium dithionite is to be compared with the plurality of mole equivalents required according to prior art splitting processes. For this reaction stage, a duration of approx 5 minutes under agitation is to be expected.

The thus obtained solution is subsequently acidified with a strong acid, preferably sulphuric acid or hydrochloric acid, to a pH level of 4.5.

At this point, the desired 5-amino salicylic acid precipitates out of the solution, while the sulphanilic acid remains in solution as its sodium salt. After filtering off and washing with water, there will be obtained a product of extremely high purity. Liquid chromatographic examinations have shown that purities of 95 percent or over can be attained according to this methodology without difficulty.

In continued acidification of the mother liquor to a pH of 3, the sulphanilic acid will precipitate and may be reused in the process. Hence, the method according to the present invention makes it possible to recover 80-85 percent of the sulphanilic acid batch, including the previously described filtering off of sodium sulphanilate.

The present invention has been defined in the appended claims and will now be described in greater detail in conjunction with a number of relevant Examples.

The following general formula applies for the reaction according to the present invention:

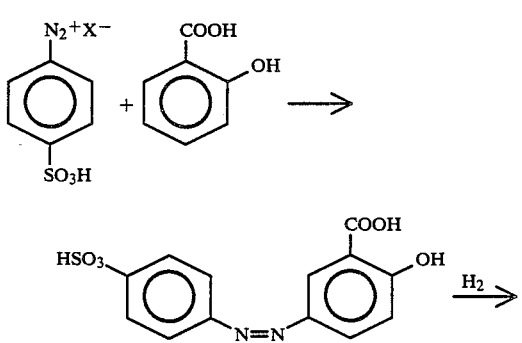

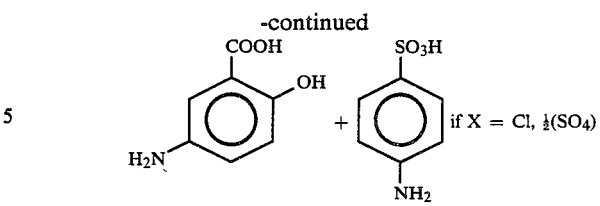

| REFERENCES AS ABOVE | |
|---|---|
| 1. Gatterman, | B. 26 1850 |
| 2. Hochst, | D.R.P. 96853 |
| 3. Beilstein, | A. 130, 243 |
| 4. Wessely, Benedikt, Benger | M. 80 (1949) 197,200 |
| 5. Fischer, Shaar-Rosenberg, | B. 32 81 |
| 6. Griess, | B. 11 2196 |
| 7. Patent application from Ferring A/S, Vanlose, Denmark | |

B = Berichte der Deutschen Chemischen Gesellschaft
M = Monatshefte fur Chemie
A = Annalen der Chemie

EXAMPLE 1

Sulphanilic acid (138.4 g, 0.80 mol) is slurried in water (192 ml) and 96 percent sulphuric acid (25 ml) is added during cooling. The reaction mixture is cooled to 5° C. Sodium nitrite (57.4 g, 0.83 mol) dissolved in water (104 ml) is slowly added (1 h) beneath the surface of the reaction mixture which maintains a temperature of 5°-10° C. When all of the sodium nitrate has been added, the temperature is allowed to rise to 10°-15° C. The thus formed diazonium salt of sulphanilic acid is used in the manner described below.

In another vessel, 46 percent sodium hydroxide sol. (100 ml) in water (184 ml) is batched and salicylic acid (112 g, 0.81 mol) is added during cooling. When all of the addition has been completed, the solution is cooled to 10° C. To this solution there is then added the above-described cooled reaction mixture with the diazonium salt of sulphanilic acid. This addition is effected under cooling and the temperature is permitted to rise from 10° C. to 22° C.

The link product, 5-(p-sulphophenyl azo)salicylic acid, is batched in an autoclave and 5 percent Pd/C (2.5 g, 54 percent moisture) is added. The mixture is heated to 75° C. and, after nitrogen gas aspiration, hydrogen gas is led in at a pressure of 5 atmospheres. When no further hydrogen gas is absorbed, the reaction is allowed to proceed after reaction under the same conditions for 0.5-1.0 hours.

The catalyst is filtered off at 60°-70° C. and sodium dithionite (2.8 g) dissolved in water (24 ml) is added. Agitation is effected at 60° C. for 5 minutes in a nitrogen gas atmosphere. The solution is cooled to 20° C. and the thus formed sodium sulphanilate is filtered off. Thereafter, the solution is reheated. Concentrated sulphuric acid (approx. 25 ml) is added at 60° C. and nitrogen gas atmosphere to a pH of 4.5. The thus formed slurry is cooled to 20° C., and the product is removed by filter suction. After washing with water (4x60 ml) and drying, there is obtained 112 g of 5-amino salicylic acid.

Liquid chromatic inspection showed that the thus obtained 5-ASA has a purity of 95 percent, which corresponds to a yield of 91 percent.

EXAMPLE 2

A corresponding experiment to that of Example 1 is also undertaken on a semi-industrial scale with 1000 times of each respective batch, but otherwise with unchanged methodology. In this case, there is obtained 143 kg of centrifuge-dry 5-amino salicylic acid at a purity, after drying, of 97 percent.

What I claim and desire to secure by Letters Patent is:

1. A method of producing 5-amino salicylic acid with sulphanilic acid as auxiliary chemical, characterized in that 5-(p-sulphophenyl azo) salicylic acid, produced by linking of the double sodium salt of the salicylic acid with a diazonium salt of sulphanilic acid, is split by hydrogenation with hydrogen gas and a catalyst at elevated pressure and temperature in excess of 50° C., whereafter the thus obtained 5-amino salicylic acid is precipitated from the mother liquor by acidification thereof.

2. The method as claimed in claim 1, characterized in using, in the splitting process, a catalyst of a transition metal.

3. The method as claimed in claim 1, characterized in that in the acidification of the mother liquor, such acidification is arrested at pH 4.5, when the 5-amino salicylic acid is precipitated, but not the sulphanilic acid.

4. The method as climed in claim 1, characterized in that the hydrogenation is carried out at an elevated presure of 1-10 atm above the atmospheric pressure.

5. The method of claim 2 wherein said transition metal is palladium or platinum.

6. The method of claim 3 wherein sulphuric acid or hydrochloric acid is used for said acidification.

7. The method of claim 3 wherein said sulphanilic acid is precipitated at a pH of 3 after precipitation of said 5-amino-salicylic acid.

* * * * *